(12) United States Patent
Prince

(10) Patent No.: US 11,517,249 B2
(45) Date of Patent: Dec. 6, 2022

(54) MULTIPLE ALLERGEN TEST APPLICATOR

(71) Applicant: Ty L. Prince, Knoxville, TN (US)

(72) Inventor: Ty L. Prince, Knoxville, TN (US)

( * ) Notice: Subject to any disclaimer, the term of this patent is extended or adjusted under 35 U.S.C. 154(b) by 0 days.

(21) Appl. No.: 17/402,413

(22) Filed: Aug. 13, 2021

(65) Prior Publication Data

US 2022/0125371 A1 Apr. 28, 2022

Related U.S. Application Data

(60) Provisional application No. 63/177,515, filed on Apr. 21, 2021, provisional application No. 63/171,995, filed on Apr. 7, 2021, provisional application No. 63/106,793, filed on Oct. 28, 2020.

(51) Int. Cl.
*A61B 5/00* (2006.01)

(52) U.S. Cl.
CPC .................................... *A61B 5/411* (2013.01)

(58) Field of Classification Search
CPC ... A61B 5/411; A61B 17/205; A61B 10/0035; A61B 17/32093; A61B 50/22; A61M 37/00; A61M 2209/045; A61M 2210/04
USPC ....... 600/556; 604/46; D24/147; 422/430, 9, 422/81
See application file for complete search history.

(56) References Cited

U.S. PATENT DOCUMENTS

| | | | | |
|---|---|---|---|---|
| 5,551,441 A | * | 9/1996 | Pitesky | A61B 17/205 600/556 |
| 5,605,160 A | * | 2/1997 | Fishman | A61B 17/205 600/556 |
| 5,671,753 A | * | 9/1997 | Pitesky | A61B 17/205 600/556 |
| 5,871,452 A | * | 2/1999 | Baker | A61B 5/411 600/556 |
| 5,931,794 A | | 8/1999 | Pitesky | |
| 6,077,229 A | * | 6/2000 | Pitesky | A61B 5/411 600/556 |
| 6,206,838 B1 | * | 3/2001 | Doll | A61B 17/205 600/556 |
| 6,554,777 B1 | | 4/2003 | Hein, Jr. | |
| 9,597,030 B2 | | 3/2017 | Smollar | |
| 2006/0178615 A1 | | 8/2006 | Ronborg et al. | |

(Continued)

*Primary Examiner* — Alex M Valvis
*Assistant Examiner* — Chanel J Jhin
(74) *Attorney, Agent, or Firm* — Gerald R. Black, esq.

(57) ABSTRACT

The multiple allergen testing system includes an applicator and a fluid tray. The fluid tray is cooperatively engageable with the applicator. The applicator has an allergen loading position and an allergen deposition position. In the allergen loading position, a different allergen is loaded onto each respective scratching barb from each respective reservoir of the loading tray. Each scratching barb is designed to retain a trace of allergen fluid. A pair of finger grips are positioned on opposing sides of the applicator frame. The applicator fits into one hand of a medical technician administering the allergen skin testing. The applicator is removed from the fluid tray and repositioned onto the skin of the patient. The applicator is made of compressible material. In the allergen deposition position, the applicator is compressed, and each allergen is deposited into each respective scratch generated by each respective scratching barb on the skin for further analysis.

28 Claims, 12 Drawing Sheets

(56) References Cited

U.S. PATENT DOCUMENTS

2009/0118638 A1    5/2009  Schindlbeck et al.
2017/0281158 A1*  10/2017  Lear .................. A61B 17/0644

* cited by examiner

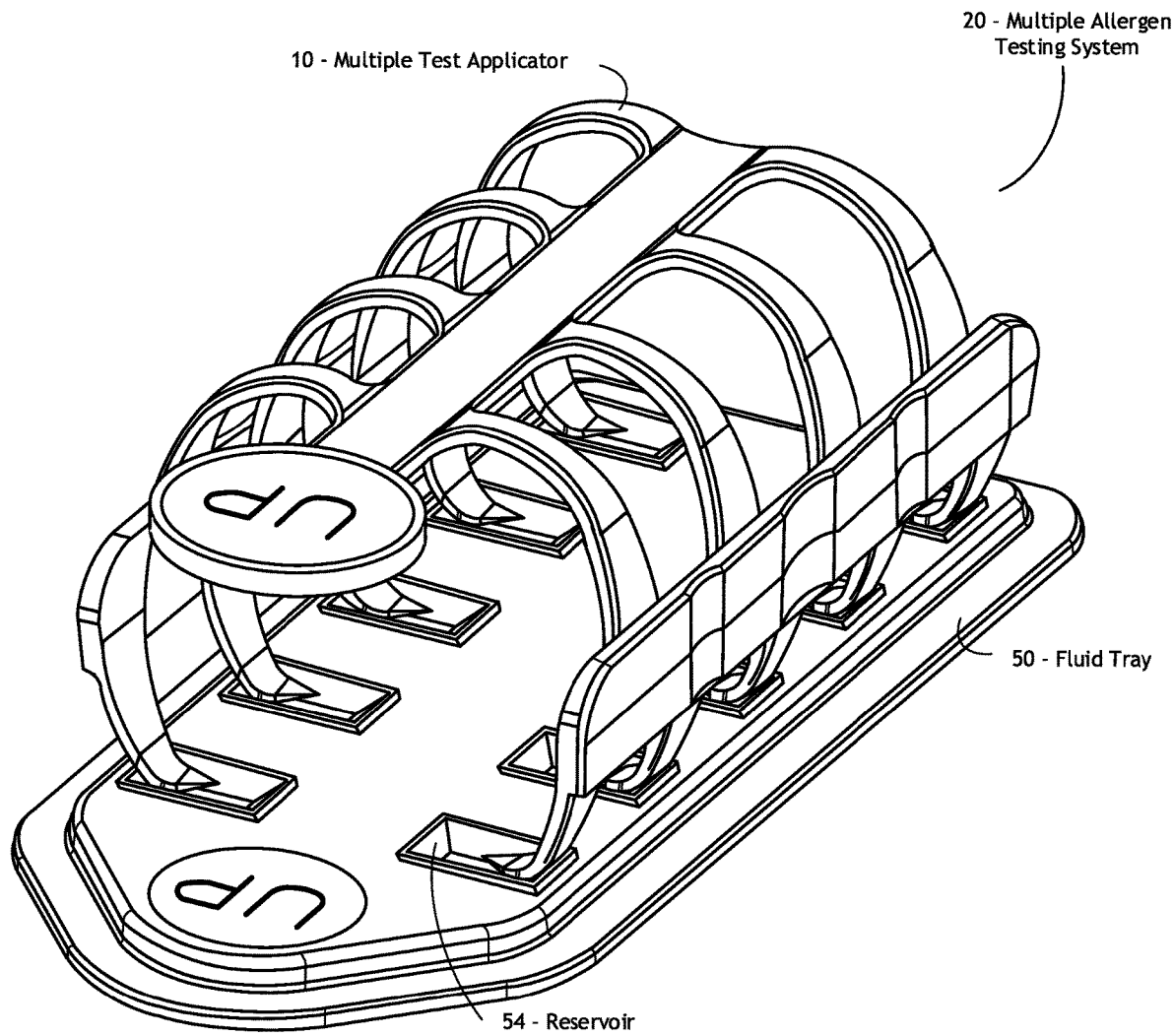
FIGURE 1
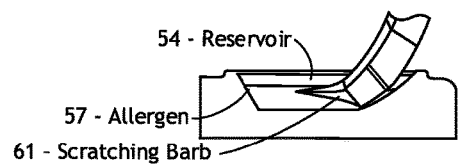
DETAIL "A"

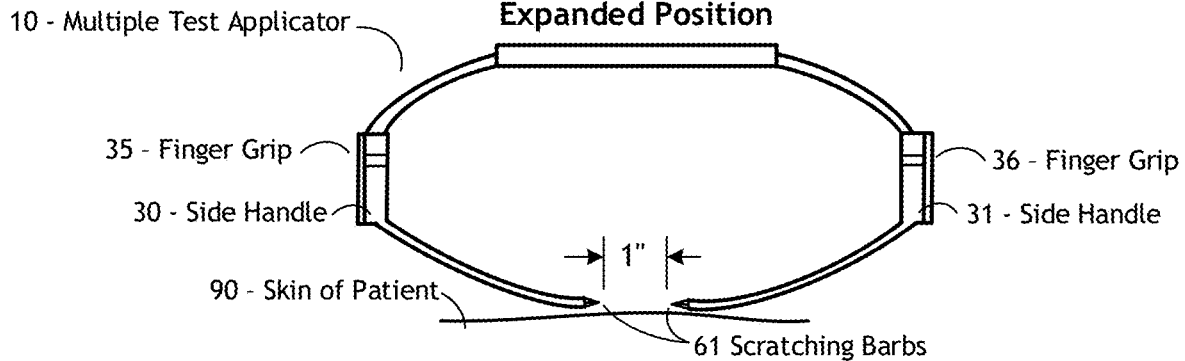
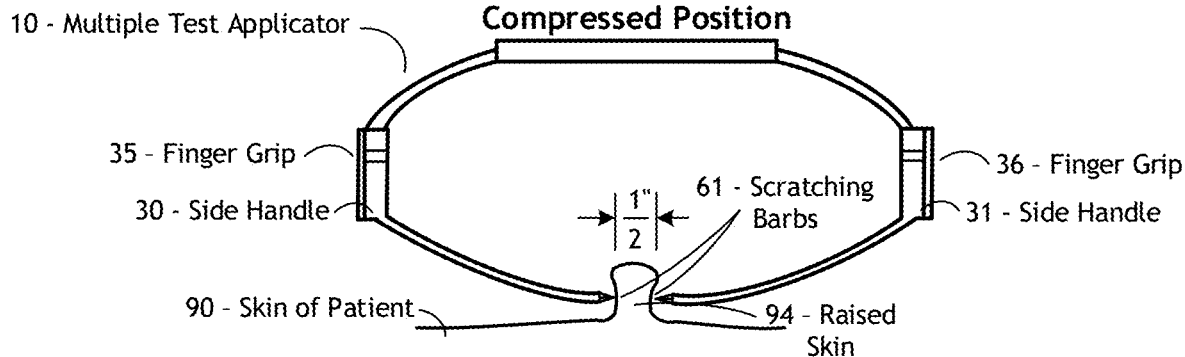
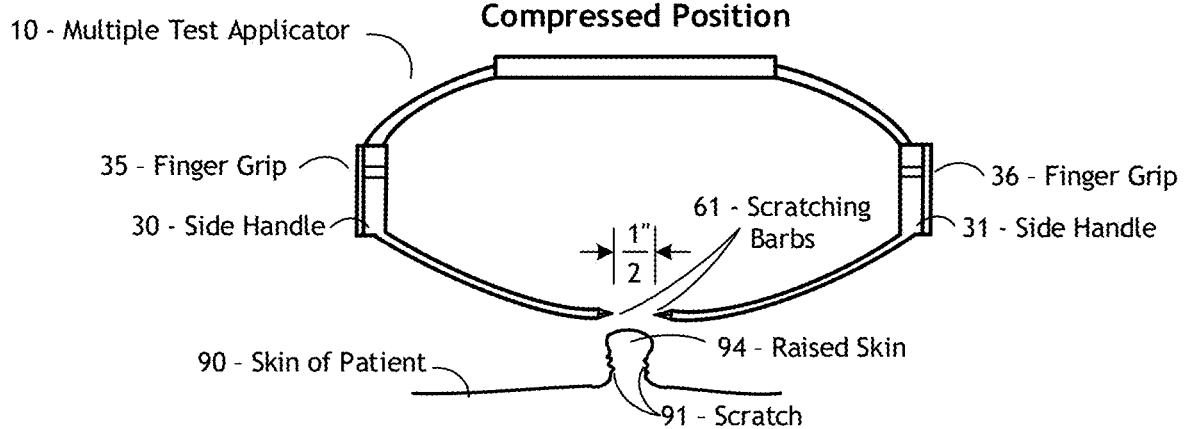

BARB TILTED UP

BARB TILTED UP

BARB TILTED UP

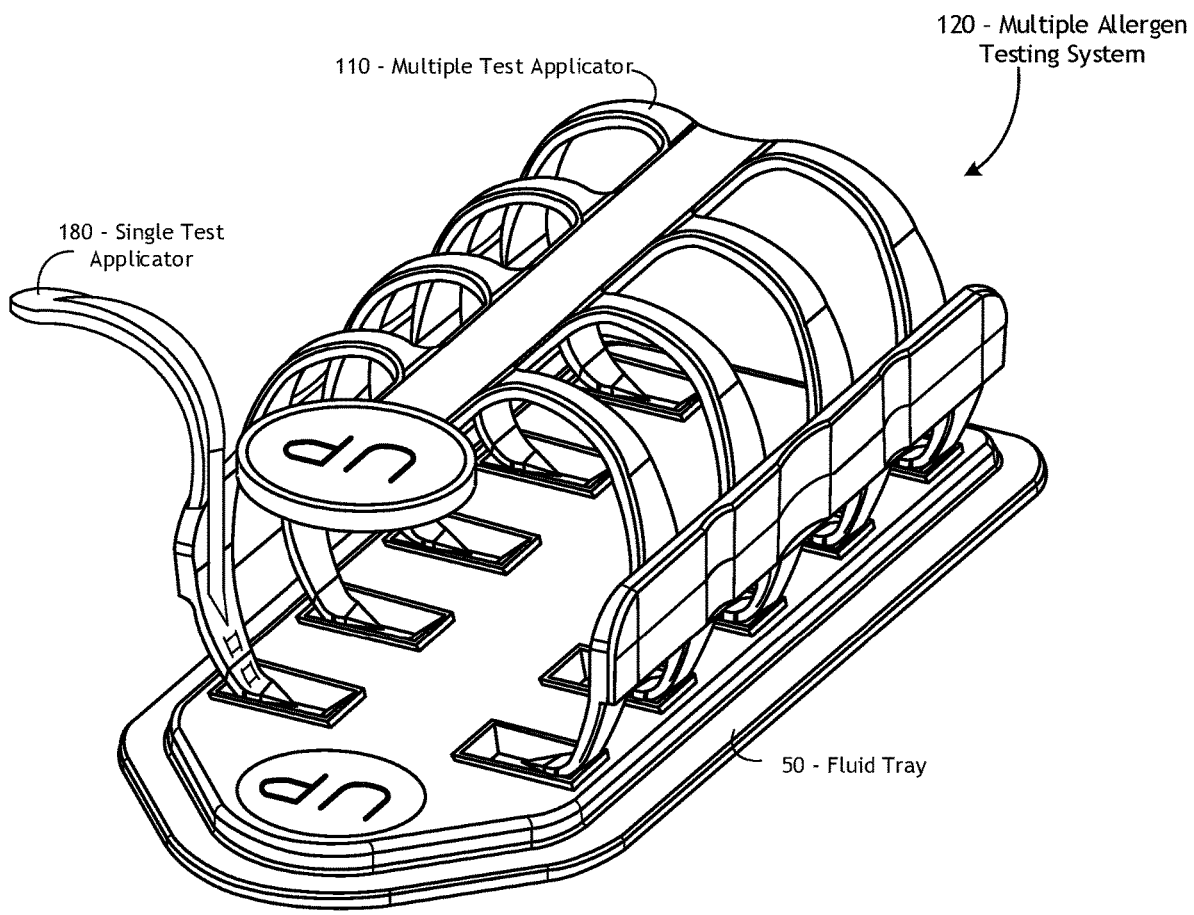
FIGURE 8
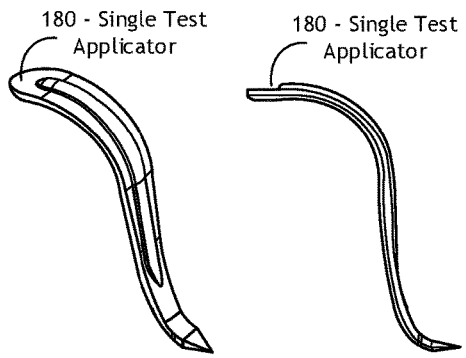
FIGURE 9A   FIGURE 9B

DETAIL "B"

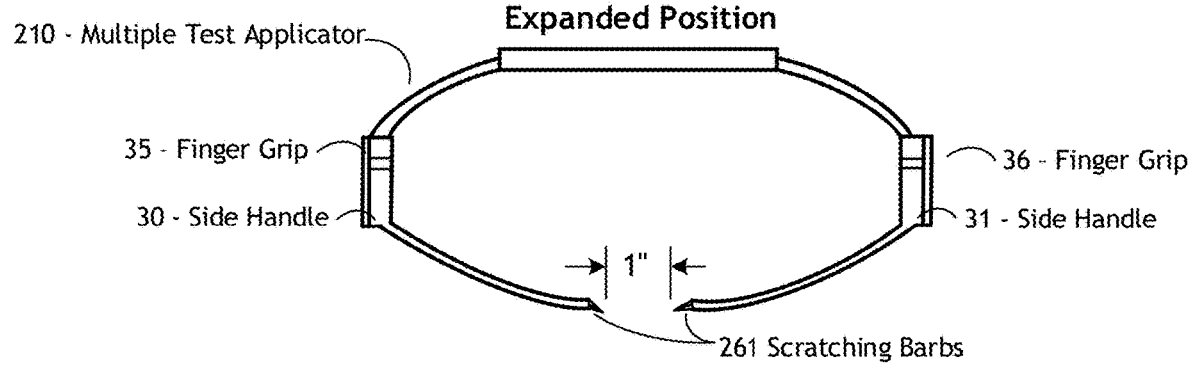
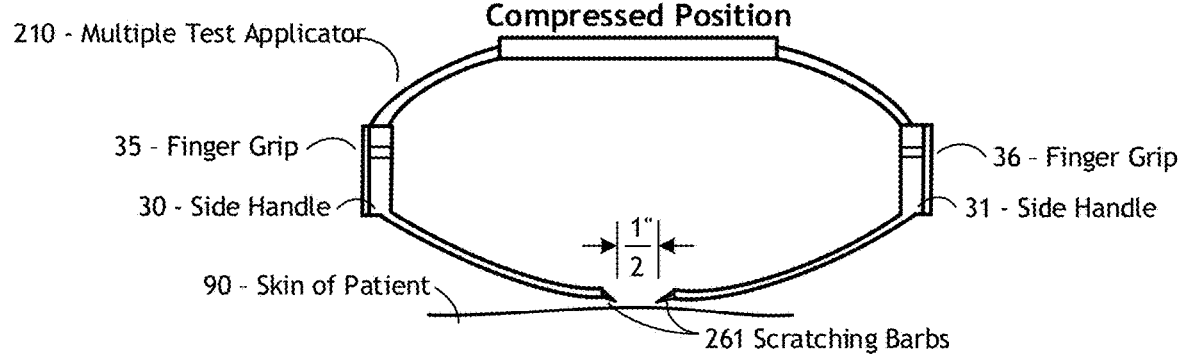
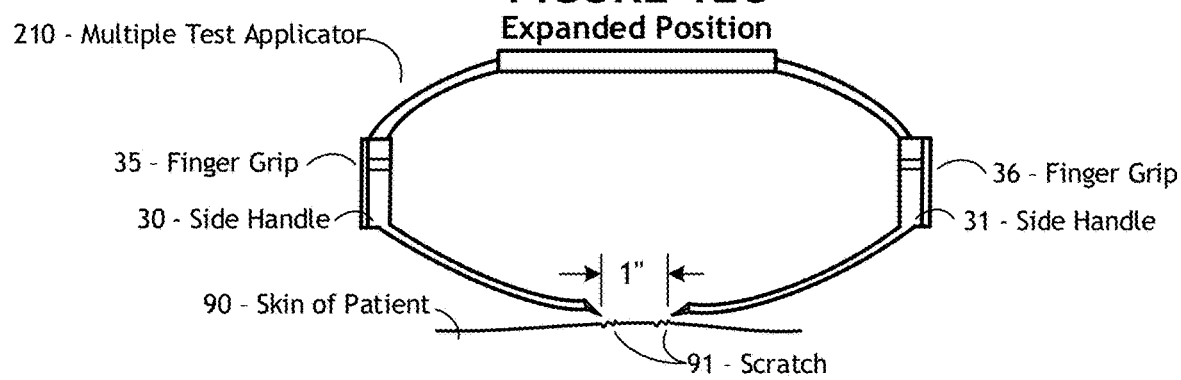

BARB TILTED DOWN

BARB TILTED DOWN

BARB TILTED DOWN

MULTIPLE ALLERGEN TEST APPLICATOR

CROSS-REFERENCE TO RELATED APPLICATIONS

This Application is a continuation-in-part to and claims priority to U.S. Provisional Application No. 63/177,515, entitled "Single and Multiple Allergen Testing System" (Prince), filed on Apr. 21, 2021; U.S. Provisional Application No. 63/171,995, entitled "Penicillin Allergy Test Kit" (Prince and Novak), filed on Apr. 7, 2021; U.S. Provisional Application No. 63/142,150, entitled "Sharps Disposal System" (Prince and Novak), filed on Jan. 27, 2021; U.S. Provisional Application No. 63/124,943 entitled "Automated Allergy Office" (Prince) filed: on Dec. 14, 2020; and U.S. Provisional Application No. 63/106,793, entitled "Single and Multiple Allergen Skin Testing System" (Prince) filed on Oct. 28, 2020.

FIELD OF USE

The present invention relates to a new multiple allergen testing system which is designed for applying and the testing and using of multiple allergens onto the skin of a patient, and more particularly, to devices, methods, and systems for conducting multiple allergy scratch tests.

BACKGROUND OF THE INVENTION

There is an increasing population of allergy disease sufferers. Accordingly, there is a growing need to address allergy medical issues, and to reduce the cost attributable to specialists being required to manage this population.

The medical technician administering these skin tests may often need to apply a relatively large number of different allergens to the skin of a patient. To perform skin tests of this type, the medical technician removes the skin-test devices, with a small amount of allergen deposited on the sharp pointed testing tip and applies the allergen to the patient in a predetermined sequence.

Some of the prior art includes:

U.S. Pat. No. 6,554,777 (Hein, Jr.) discloses a multi-site skin-test system. The system includes a reservoir tray and strips of interconnected reservoir caps inserted into upper portions of the reservoirs. The caps each include a generally conically shaped hole. Connection members connect the caps of a strip to one another. The strips of caps are pressed into tightly fitting upper portions of reservoirs having upwardly facing ledge surfaces for supporting downwardly facing bottom surfaces of the caps. The outer side surfaces of the caps and the inner surfaces of the upper portions of the reservoirs are substantially the same size to provide a tight fit. A tray lid includes a downwardly extending ridge that cooperates with the tray to prevent the lid from being placed onto the tray backwards.

U.S. Pat. No. 9,597,030 (Smollar) depicts an allergy testing kit containing a plurality of allergy testing applicators, an allergy testing tray, and a plurality of allergen bottles each containing an allergen. Each of the applicators contains an elongated handle, a plurality of arms extending from the elongated handle and disposed in an asymmetrical configuration, and a plurality of legs with tines extending from each of the arms. The allergy testing tray contains a main body having an underside and a top surface, a cover for locking with the main body and a plurality of reservoirs extending from the underside of the main body. The reservoirs each have a chamber with an opening extending from the top surface. The reservoirs are disposed in different groups and each group has an asymmetrical configuration matching that of the applicator.

U.S. patent application Ser. No. 11/885,086 (Schindlbeck; et al.) depicts a device for performing an allergy test. The device comprises a container assembly including several containers designed to receive the allergens, and a mark transferable onto the skin which is used to associate specific allergens to specific allergy sites on the skin of a living being undergoing an allergy test. The device aims at improving so that the allergy test sites on the skin can be constantly marked very legibly, and so that the corresponding marks can be readily eliminated from the skin immediately after the allergy test.

U.S. patent application Ser. No. 10/558,943 (Ronborg; et al.) discloses an allergy tester for delivering a diagnostic agent to the skin or mucosa of a patient. A chamber filled with the diagnostic agent is separate from the housing with a rod capable of transferring the diagnostic agent to the animal. The chamber is connected to the housing with the rod before transfer of diagnostic agent. In particular, the invention relates to a device for delivering allergens in allergy tests.

It is not uncommon that fifty or more different allergens will need to be screened for a particular patient. Accordingly, it becomes necessary to minimize patient discomfort while accumulating patient information so that a course of treatment can be prescribed.

What is needed is an applicator that will replace needle pricks commonly used for multiple allergy skin testing: a simple, economical, and reliable scratch testing device in which multiple allergens can be tested simultaneously on the skin of a patient which minimizes any cross contamination of allergens, while simplifying the handling of the applicator device and providing results that are easily observable.

A system is needed that significantly reduces the possibility of errors in reading the test results, while minimizing the amount of allergy testing fluid used, while reducing the contamination and false positives, and minimizing patient discomfort, which is cost-effective, and is easy to use and manufacture.

Certain other objects and advantages of the invention will become apparent from the following description of preferred embodiments of the invention taken in connection with the accompanying drawings.

SUMMARY OF THE INVENTION

The multiple allergen test applicator of the present invention addresses these needs.

For allergies to initially develop, the body must be exposed to an allergen, that prompts the body to initiate an immune response.

In intradermal skin testing, a medical professional injects a tiny amount of allergen into the outer layer or epidermis of the patient. The immediate positive skin reaction reaches a peak in about fifteen minutes, and is a pale central area surrounded by redness (a flare) and a bump or swelling (a wheal).

In addition to the allergens in question, skin testing is also performed with a positive control (histamine) that should always cause a skin reaction, and a negative control (saline), that should not cause a reaction. A test is positive if the allergen causes a wheal 3 mm greater than the negative control, and if the skin has a response to the histamine, as well.

The allergic reaction is measured immediately after the application of the allergen. The information is a direct measure of the allergy reaction occurring under the skin. The information on each site is presented to the physician to compare against visual observations. A determination of the patient susceptibility to each allergen is determined by the physician and a course of future action is planned. A positive skin test does not predict the severity of an allergic reaction. A negative skin test usually means the patient is not allergic.

In general, allergy skin tests are reliable for diagnosing allergies to airborne substances, such as pollen, pet dander and dust mites. Skin testing may help diagnose food allergies, but because food allergies can be complex, additional procedures may be required.

The multiple allergen testing system is removed from its sterile package. The multiple allergen testing system includes the multiple test applicator of the present invention and a fluid tray.

Allergens are put into containment reservoirs in the fluid tray, and care is taken not to use an excess amount of the allergens.

The multiple test applicator of the present invention is cooperatively engageable with the fluid tray. The multiple test applicator and fluid tray are designed to minimize any cross contamination of the various allergens.

The multiple test applicator has an allergen loading position and an allergen deposition position, the multiple test applicator is made of compressible material.

The scratching barbs are pointed upward and are placed in their respective reservoirs in the fluid tray with each respective scratching barb contacting a different fluid reservoir. In the allergen loading position, a different allergen is loaded onto each respective scratching barb from each respective reservoir of the loading tray. Each respective scratching barb contacts a small amount of each respective allergen in each respective reservoir. Each scratching barb is designed to retain a trace amount of allergen fluid which is subsequently delivered under the epidermis of the patient.

The multiple test applicator of the present invention is preferably sized to be held in one hand of a medical technician administering the allergen skin testing. A pair of finger grips are positioned on opposing sides of the applicator frame.

Once allergen loading is complete, the multiple test applicator is removed from the fluid tray and repositioned onto the skin (i.e.—arm, back, or leg) of the patient for allergen deposition.

The two side handles of the multiple test applicator of the present invention are squeezed towards each other lifting the skin between the two sides of the multiple test applicator.

The scratching barbs contact both sides of the raised skin, the skin is raised by the skin lifting pads on both sides of the barb, the skin lifting pads also limit the depth that the barb can penetrate the skin, as the applicator generates scratches at the test site by moving the applicator upward or downward, as trace amounts of each respective allergen flows into each respective scratch. The multiple test applicator is manipulated to make a small scratch at each test site. Then the multiple test applicator is pulled up and away from the skin. After the testing has been completed, the physician analyzes the test results to determine the next course of action.

In an alternative embodiment, the scratching barbs are pointed downward. After completing allergen loading in the expanded position, the scratching barbs are removed from the fluid tray and the applicator is compressed and placed on the skin of the patient and released. The downward projecting scratching barbs will generate a plurality of respective scratches as each respective allergen is deposited into each respective scratch enabling one-handed operation.

For a complete understanding of the multiple allergen test applicator of the present invention, reference is made to the accompanying drawings and description in which the presently preferred embodiments of the invention are shown by way of example.

As the invention may be embodied in many forms without departing from spirit of essential characteristics thereof, it is expressly understood that the drawings are for purposes of illustration and description only and are not intended as a definition of the limits of the invention.

BRIEF DESCRIPTION OF THE DRAWINGS

FIG. 1 depicts an assembly view of a first preferred embodiment of an allergy testing system comprising a first preferred embodiment of the multiple test applicator of the present invention having ten applicators cooperatively engaged with a fluid tray, the multiple test applicator being disposed on the fluid tray; and DETAIL "A" depicts an exploded side view of the scratching barb positioned in a reservoir of the fluid tray during allergen loading, the reservoir being partially filled with allergen.

FIG. 5A is a front view of the multiple test applicator of FIG. 1, the multiple test applicator being in an expanded position, the scratching barbs resting upon the skin of a patient.

FIG. 5B is a front view of the multiple test applicator of FIG. 5A, the multiple test applicator now being in a compressed position, the scratching barbs resting upon the skin of a patient with each of the opposed scratching barbs disposed at two test sites of a patient, with the skin having been lifted upwards between the pair of opposed scratching barbs.

FIG. 5C is a front view of the multiple test applicator of FIG. 5B, the multiple test applicator still being in a compressed position, the scratching barbs now being raised from the skin of the patient with scratches now appearing on each side of the raised skin of the patient.

FIG. 8 depicts an assembly view of a second preferred embodiment of an allergy testing system comprising a second preferred embodiment of the multiple test applicator of the present invention having nine scratching barbs, and a single test applicator with a single scratching barb, all being cooperatively engaged with ten fluid reservoirs in a fluid tray.

FIG. 9A depicts an assembly view of the single test applicator of FIG. 8, and FIG. 9B depicts an end view of the single test applicator of FIG. 8A.

FIG. 12A is a front view of the multiple test applicator of the present invention [210] in an expanded position, with the scratching barbs, the scratching barbs now being loaded, and each include a trace of their respective allergens and are prepared for allergen deposition.

FIG. 12B is a front view of the multiple test applicator of FIG. 12A, the multiple test applicator now being in a compressed position. The scratching barbs are resting upon the skin of a patient with the each of two scratching barbs pointed downward.

FIG. 12C is a front view of the multiple test applicator of FIG. 12B, the multiple test applicator now being in an expanded position, the scratching barbs now have generated a pair of scratches at a pair of test sites as the scratching barbs move away from each other.

DETAILED DECRIPTION OF THE PREFERRED EMBODIMENTS

Figure 2:
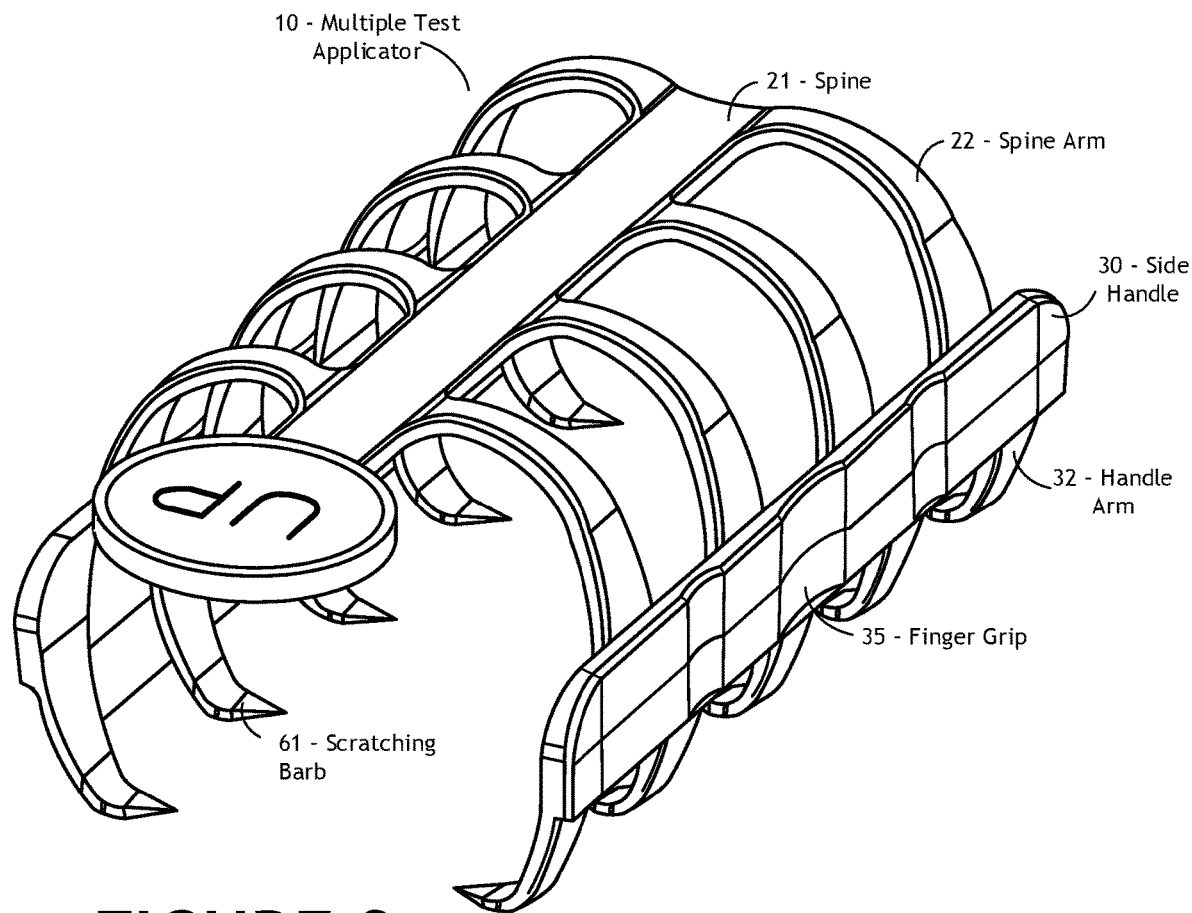
FIG. 2 depicts the first preferred embodiment of the multiple test applicator of the present invention as shown in FIG. 1.

Referring now to the drawings, FIG. 1 depicts an assembly view of a first preferred embodiment of an allergy testing system [20] comprising of a first preferred embodiment of the multiple test applicator of the present invention [10] having ten applicators cooperatively engaged with a fluid tray [50]. The multiple test applicator [10] is cooperatively engageable with the ten allergen reservoirs [54], each one retaining a different liquid for allergen skin testing.

The multiple test applicator of the present invention [10] has an allergen loading position and an allergen deposition position.

DETAIL "A" is an exploded side view of a scratching barb [61] positioned in a reservoir [54] of the fluid tray [50], the reservoir [50] being partially filled with allergen [57]. DETAIL "A" depicts the multiple test applicator of the present invention [10] in the allergen loading position. During allergen loading, the scratching barbs [61] are dipped into the allergen [57] setting in the reservoirs [54].

FIG. 2 depicts the first preferred embodiment of the multiple test applicator of the present invention [10] as shown in FIG. 1. Each of the ten scratching barbs [61] is cooperatively engageable with one of the ten reservoirs [54] of the fluid tray [50] and has a slight upward tilt.

Allergens [57] are placed into respective reservoirs in the fluid tray [50]. Care is taken to avoid using excess amounts of allergens [57] which may cause cross contamination of allergens.

The size of the reservoirs [54] and the distance between adjacent reservoirs [54] are designed to minimize any cross contamination of the allergens [57].

In the allergen loading position, a different scratching barb [61] is positioned into each respective reservoir [54] of the loading tray [50]. Each scratching barb [61] contacts a small amount of the allergen [57] in each respective reservoir [54]. Each scratching barb [61] retains a trace amount of allergen [57] in the allergen loading position which is deposited under the epidermis of the patient in the allergen deposition position.

The multiple test applicator [10] includes a pair of opposing side frames or handles [30 and 31]. A finger grip [35 or 36] is positioned on each side frame or handle [30 and 31]. As the finger grips [35 and 36] are squeezed together for allergen deposition, the multiple test applicator [10] is compressed and the distance between the first and second scratching barbs [61] decreases.

Figure 3:
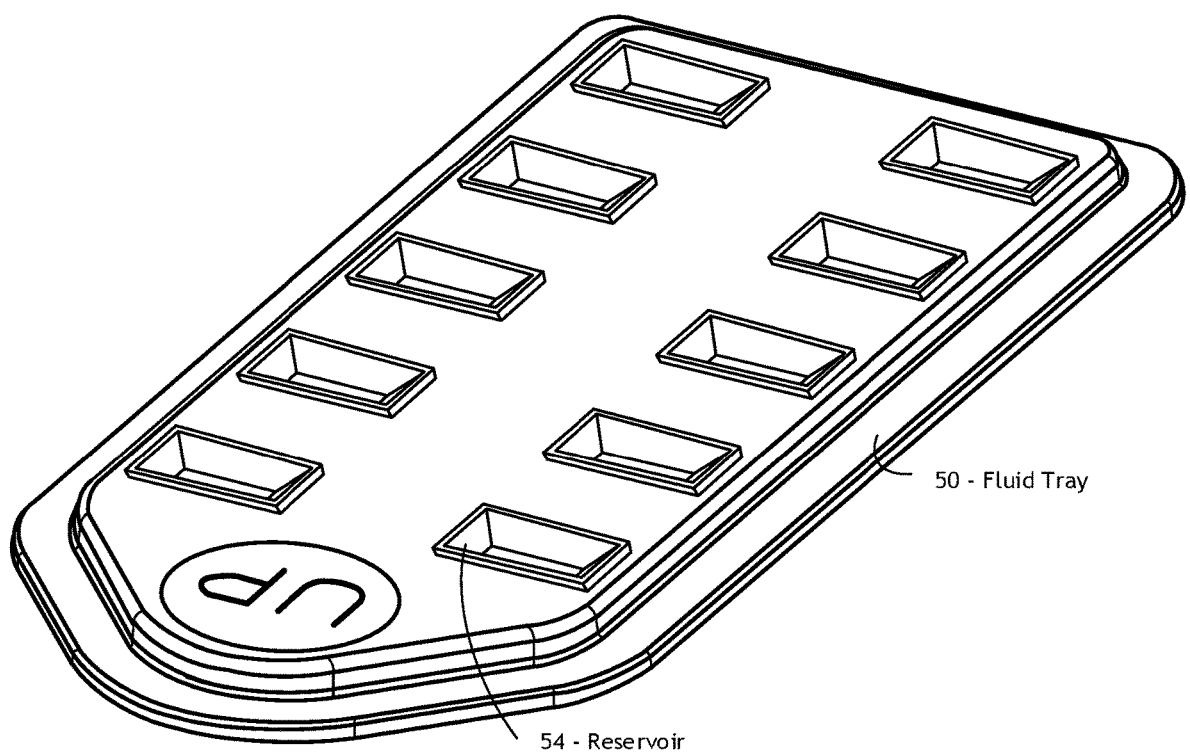
FIG. 3 depicts a detailed assembly view of the fluid tray of FIG. 1 complete with ten reservoirs.

FIG. 3 depicts a detailed assembly view of the fluid tray [50] of FIG. 1 complete with ten reservoirs [54].

The multiple test applicator is made of compressible material. The materials of choice are engineering grade polymers, since the multiple test applicator needs to be sterilized in an autoclave prior to use, the material must be stable at elevated temperatures.

Figure 4:
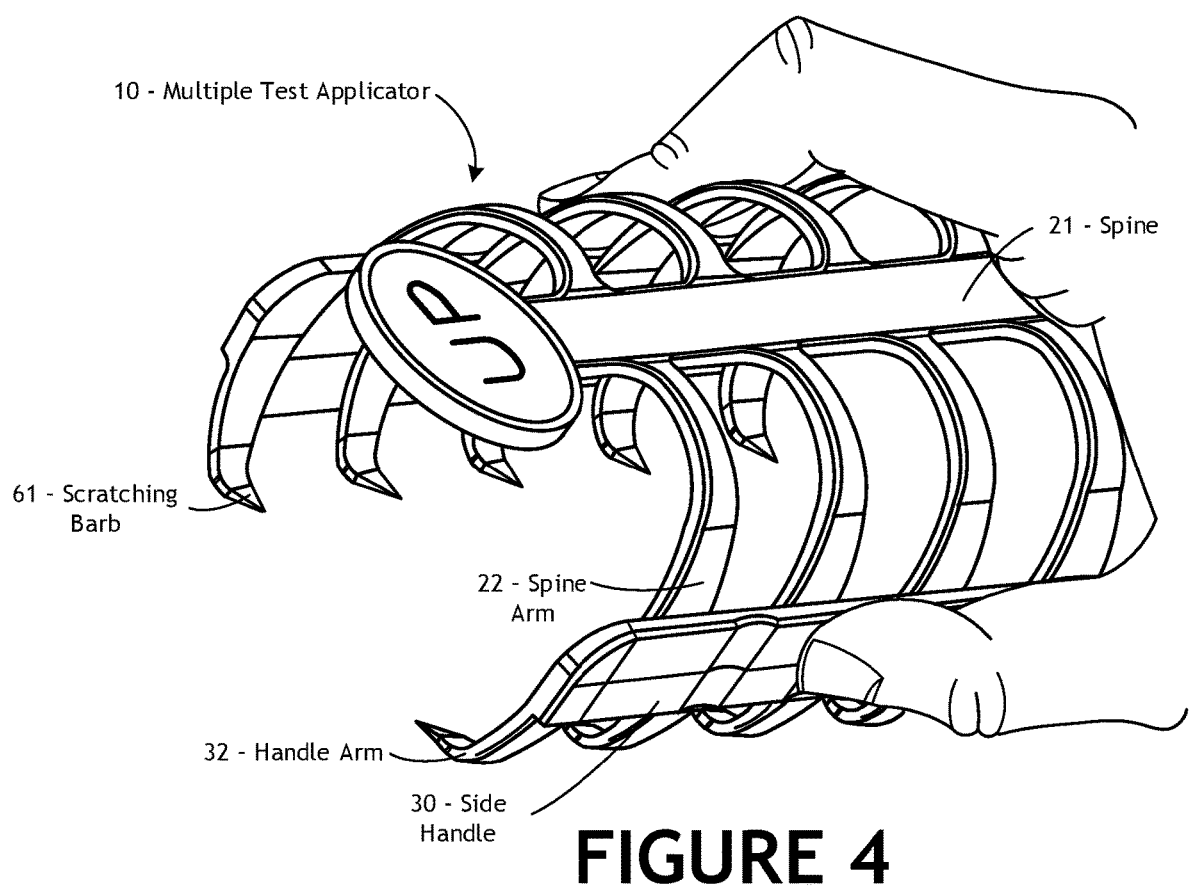
FIG. 4 depicts the first preferred embodiment of the multiple test applicator of the present invention of FIG. 2 held in one hand of a medical technician, with the thumb positioned on a first finger grip on a first side frame and the index finger positioned on a second finger grip on a second side frame, the first side frame opposing the second side frame.

FIG. 4 depicts the first preferred embodiment of the multiple test applicator of the present invention [10] of FIG. 2 held in one handoff a medical technician, with the thumb positioned on a finger grip on a first side handle [30] and the index finger [35] positioned on a second finger grip [36] on a second side handle [31], the second side handle [31] opposing the first side handle [30]. The multiple test applicator of the present invention [10] is preferably sized to be held in one hand of a medical technician administering the allergen skin testing.

It is critical that the multiple test applicator [10] be held in one hand of the medical technician who is administering the test. This enables the other hand to be free to take notes, to assist the patient, or do whatever becomes else necessary during the administration of the procedure.

FIG. 5A is a front view of the multiple test applicator of the present invention [10] in an expanded position, with the scratching barbs [61] resting upon the skin of a patient [90]. The scratching barbs [61] each include a trace of their respective allergens and are prepared for allergen deposition.

FIG. 5B is a front view of the multiple test applicator of the present invention [10]. The multiple test applicator is now being in a compressed position by use of the pair of finger grips [35 and 36]. The scratching barbs [61] are resting upon the skin of the patient [90] with the each of two scratching barbs [61] disposed about a portion of the skin of a patient [90] that has been lifted upwards [94] between the pair of opposed scratching barbs [61]. The multiple test applicator [10] is in the allergen deposition position.

The multiple test applicator [10] includes a pair of opposing scratching barbs [61], one scratching barb [61] on each side handle [30 and 31]. As the two side handles [30 and 31] are squeezed together, the scratching barbs [61] are repositioned relative to each other.

FIG. 5C is a front view of the multiple test applicator of FIG. 5B. The multiple test applicator [10] is still being compressed. The scratching barbs [61] now have been raised upward from the skin of the patient [90] with a pair of scratches [61] now appearing on each side of the portion of the skin of the patient that was lifted upwards [94].

Figure 6A:
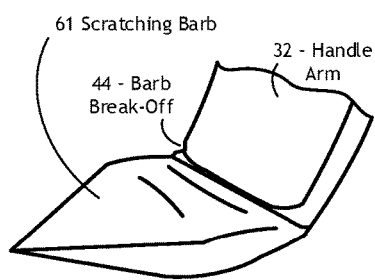
FIG. 6A is an exploded assembly view of the first preferred embodiment of the scratching barb pointed upward toward the spine of the multiple test applicator of FIG. 1, a tip break-off section is also depicted.

FIG. 6A is an exploded assembly view of the first preferred embodiment of the scratching barb pointed upward [61] toward the spine [21] of the multiple test applicator [10]. A barb break-off section [45] is also shown.

Figure 6B:
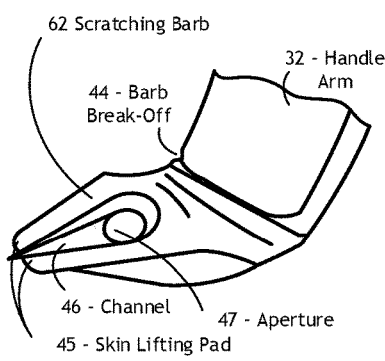
FIG. 6B is an exploded assembly view of a second preferred embodiment of the scratching barb pointed upward toward the spine of the multiple test applicator of FIG. 1, the scratching barb including an aperture and a channel for retaining a trace amount of the allergen, a tip break-off section is also depicted. Skin lifting pads are shown on both sides of the barb, they lift the skin and limit the depth of the scratching barb.

FIG. 6B is an exploded assembly view of a second preferred embodiment of the scratching barb pointed upward [62] toward the spine [21] of the multiple test applicator [10]. The scratching barb [62] includes an aperture and a channel for retaining a trace amount of the respective allergen [57]. A barb break-off section [45] is also shown. A pair of skin lifting pads [45] are sandwiched about each scratching barb [61]. The pair of skin lifting pads [45] lift the skin and limit the depth of the scratching barb. The pair of skin lifting pads [45] control the depth of the penetration of the scratching barbs [61] and also ensure repeatability of the testing.

Figure 6C:
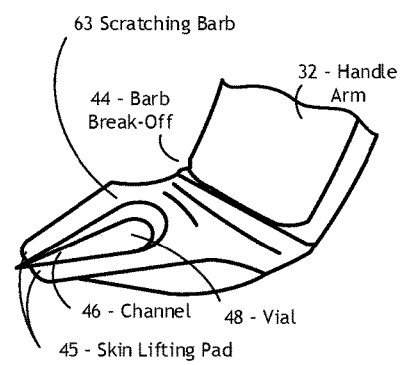
FIG. 6C is an exploded assembly view of a third preferred embodiment of the scratching barb pointed upward toward the spine of the multiple test applicator of FIG. 1, the scratching barb including a vial and a channel for retaining a trace amount of the allergen, a tip break-off section is also depicted. Skin lifting pads are shown on both sides of the barb, they lift the skin and limit the depth of the scratching barb.

FIG. 6C is an exploded assembly view of a third preferred embodiment of the scratching barb pointed upward [63] toward the spine [21] of the multiple test applicator [10]. The scratching barb includes a vial and a channel for retaining a trace amount of the respective allergen [57]. A barb break-off section [44] is also shown. A pair of skin lifting pads [45] are sandwiched about each scratching barb [61]. The pair of skin lifting pads [45] lift the skin and limit the depth of the scratching barb. The pair of skin lifting pads [45] control the depth of the penetration of the scratching barbs [61] and ensure repeatability of the testing.

Figure 7:
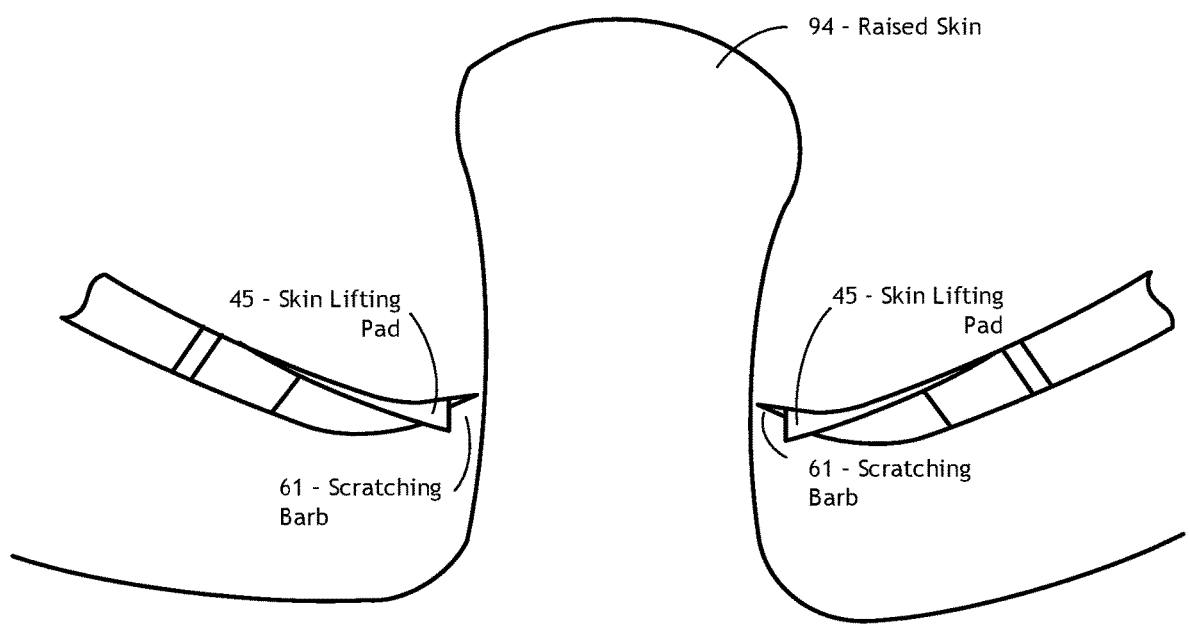
FIG. 7 depicts an exploded side view of a pair of scratching barbs being raised upward on a portion of the skin of a patient that has been pulled together to prepare the site for a pair of scratches from the pair of scratching barbs, a pair of skin lifting pads being positioned, one on each side of each skin scratching barb, that lift the skin and limit the depth of penetration of each scratching barb.

FIG. 7 depicts an exploded side view of a pair of scratching barbs [61] being raised upward on a portion of the skin of a patient that has been pulled together and raised [94] to prepare the site for a pair of scratches [91] from the pair of scratching barbs. Skin lifting pads [45] are shown on both sides of the barb, they lift the skin and limit the depth of the scratching barb.

FIG. 8 depicts an assembly view of a second preferred embodiment of an allergy testing system [120] comprising a second preferred embodiment of the multiple test applicator of the present invention [110] having nine scratching barbs, and a single test applicator [180] with a single scratching barb, all being cooperatively engaged with ten fluid reservoirs in a fluid tray [50]. The multiple test applicator of the present invention is also compatible with multiple single test applicator units [180] when aligned with a fluid tray that is properly sized with the number and alignment of fluid reservoirs (not shown).

FIG. 9A depicts an assembly view of the single test applicator [180] of FIG. 8, and FIG. 9B depicts an end view of the single test applicator [180] of FIG. 8A.

Figure 10:
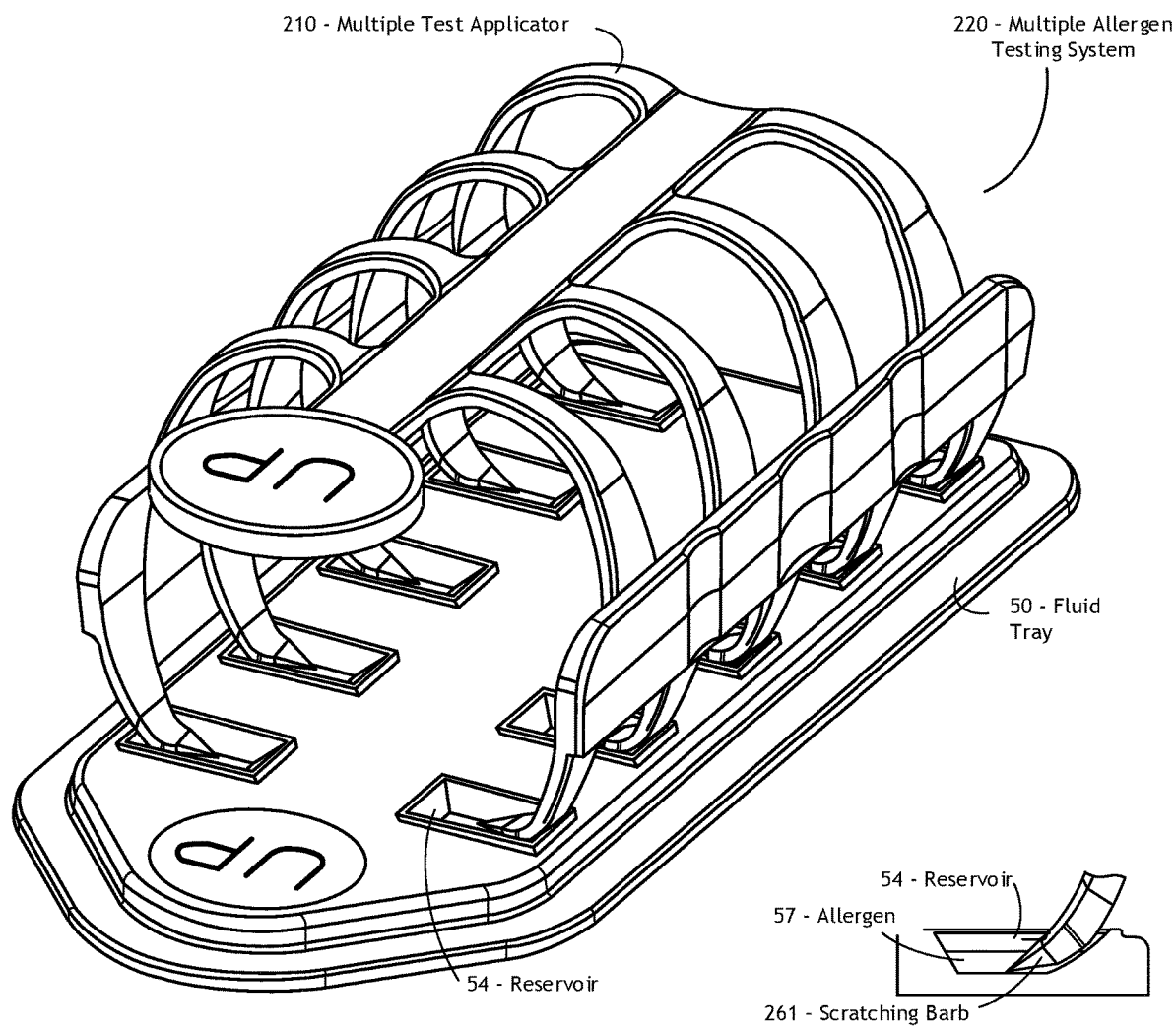
FIG. 10 depicts an assembly view of a third preferred embodiment of an allergy testing system comprising of a third preferred embodiment of the multiple test applicator of the present invention having ten applicators cooperatively engaged with a fluid tray, the multiple test applicator being disposed on a fluid tray; and DETAIL "B" depicting an exploded side view of the scratching barb positioned in a reservoir of the fluid tray, the reservoir being partially filled with allergen.

FIG. 10 depicts an assembly view of a third preferred embodiment of an allergy testing system [220] comprising of a third preferred embodiment of the multiple test applicator of the present invention [210] having ten applicators cooperatively engaged with a fluid tray [50]. DETAIL "B" depicts an exploded side view of the scratching barb [261] positioned in a reservoir [54] of the fluid tray [50], the reservoir [54] being partially filled with allergen [57]. The scratching barbs [261] are pointed downward. DETAIL "B" depicts the multiple test applicator of the present invention [110] in the allergen loading position.

Figure 11:
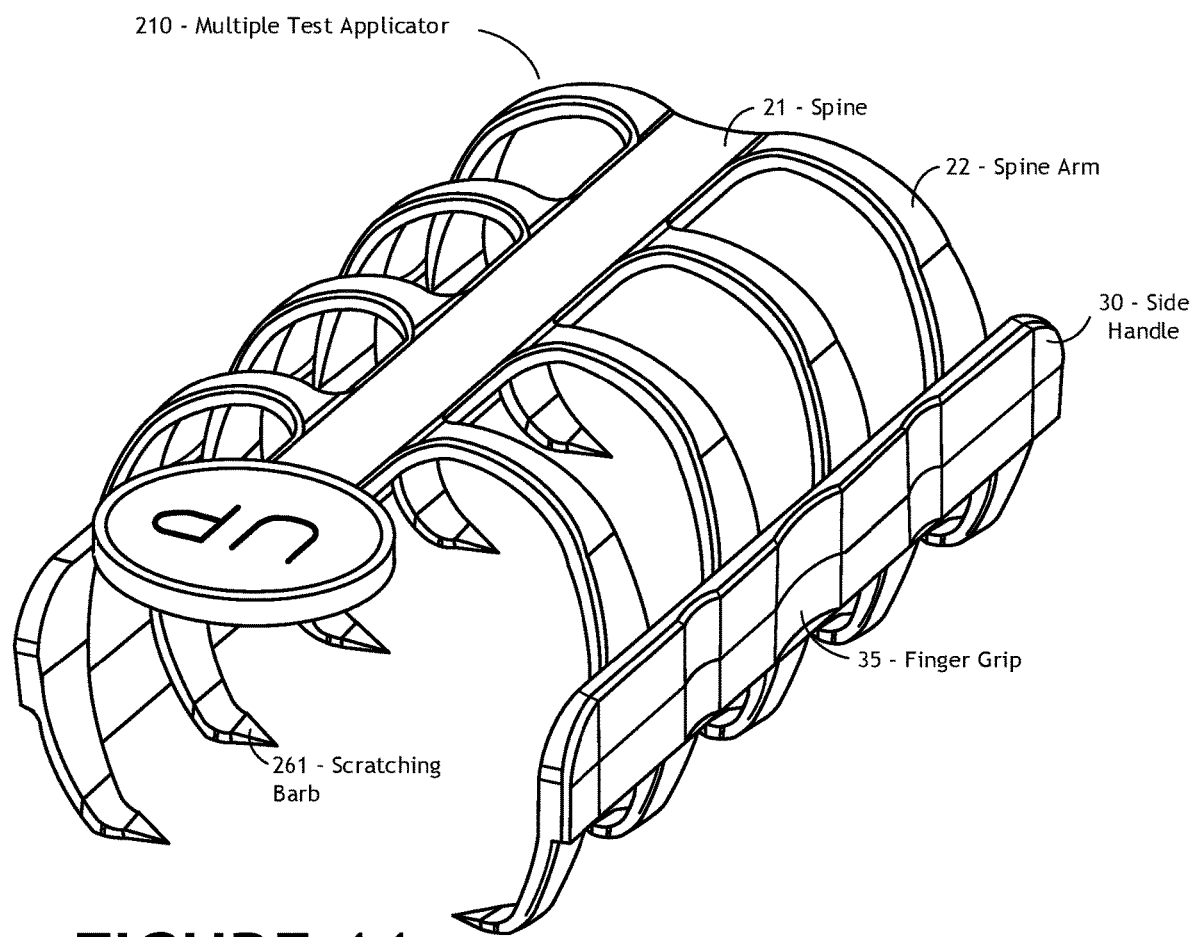
FIG. 11 depicts the first preferred embodiment of the multiple test applicator of the present invention as shown in FIG. 10.

FIG. 11 depicts the first preferred embodiment of the multiple test applicator of the present invention [210].

FIG. 12A is a front view of the multiple test applicator of the present invention [210] in an expanded position, with the scratching barbs [61]. The scratching barbs [61] have been loaded and each include a trace of their respective allergens and are prepared for allergen deposition.

FIG. 12B is a front view of the multiple test applicator of FIG. 12A, the multiple test applicator now being in a compressed position. The scratching barbs [261] are resting upon the skin of a patient [90] with the each of two scratching barbs [261] pointed downward.

After completion of allergen loading in the expanded position, the first scratching barb [61] and the second scratching barb [62] are removed from the fluid tray [50]. The multiple test applicator [10] is moved into the compressed position and placed on the skin of the patient [90] and released.

FIG. 12C is a front view of the multiple test applicator of FIG. 12B, the multiple test applicator now being in an expanded position. The scratching barbs [61] now have generated a pair of scratches [91] on the skin of the patient [90] at a pair of test sites as the scratching barbs [61] have separated from each other.

Figure 13A:
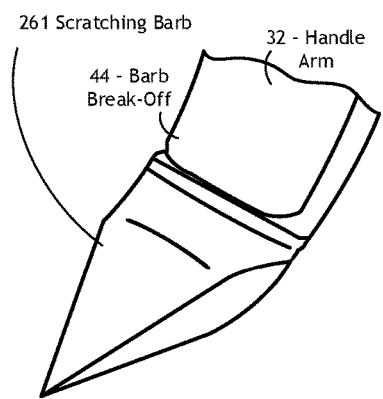
FIG. 13A is an exploded assembly view of the first preferred embodiment of the scratching barb pointed downward away from the spine of the multiple test applicator of FIG. 10, a tip break-off section is also depicted.

FIG. 13A is an exploded assembly view of the first preferred embodiment of the scratching barb [261] pointed downward away from the spine [21] of the multiple test applicator of the present invention [210]. A barb break-off section [45] also being shown.

Figure 13B:
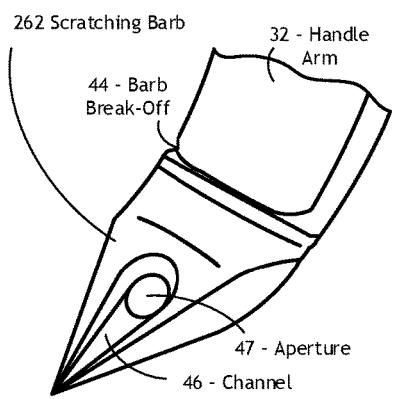
FIG. 13B is an exploded assembly view of a second preferred embodiment of the scratching barb pointed downward away from the spine of the multiple test applicator of FIG. 9, the scratching barb including an aperture and a channel for retaining a trace amount of the allergen, a tip break-off section is also depicted.

FIG. 13B is an exploded assembly view of a second preferred embodiment of the scratching barb [262] pointed downward away from the spine [21] of the multiple test applicator [210], the scratching barb [262] including an aperture [47] and a channel [46] for retaining a trace amount of the allergen [57]. A barb break-off section [45] also being shown.

Figure 13C:
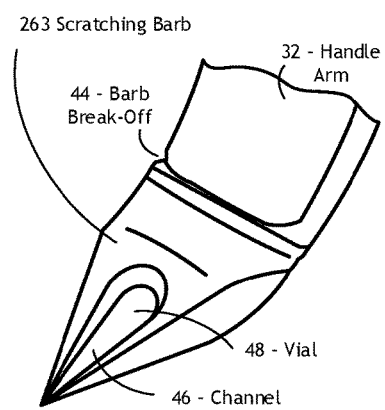
FIG. 13C is an exploded assembly view of a third preferred embodiment of the scratching barb pointed downward away from the spine of the multiple test applicator of FIG. 9, the scratching barb including a vial and a channel for retaining a trace amount of the allergen, a tip break-off section is also depicted.

FIG. 13C is an exploded assembly view of a third preferred embodiment of the scratching barb [263] pointed downward away from the spine [21] of the multiple test applicator [210], the scratching barb [263] including a vial and a channel for retaining a trace amount of the allergen [57], a break-off section also being shown. FIG. 13C depicts the multiple test applicator of the present invention [110] in the allergen deposition position. A barb break-off section [45] also being shown.

Once allergen loading is complete, the multiple test applicator of the present invention [10] is removed from the fluid tray [50] and repositioned onto the skin (i.e.—arm, back, or leg) of the patient [90].

In the allergen deposition position, the multiple test applicator of the present invention [10] is compressed, and each allergen [57] is deposited into each respective scratch [91] generated by each respective scratching barb [61] on the skin of the patient [90] for further analysis as needed by the treating physician.

After the prescribed time 10-20 minutes the test operator records the skin condition with a photo of each scratch site. The Applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The testing tray can also be disposed of in the same container. This increases the packing density of the discarded material and a much lower disposal cost.

Also, applicator [10] of the multiple allergen testing system of the present invention has the advantage of breaking the skin of the patient without downward pressure. This diminishes chances of the mast cells (histamine containing cells) releasing the histamine secondary to pressure causing a false positive. This may be a critical factor with percutaneous allergy testing.

The single and multiple allergen testing system enables testing for a single allergy or multiple allergies in the same device. The allergen testing applicator of the present invention simulates the best practice in a controlled procedure. The multi-allergen testing system is designed around a multiple allergen testing device that enables the accurate and repeatable placement of allergy testing fluid, either in a tray or on the skin of a patient. The testing procedure also controls the scratching or pricking of the skin, to introduce the allergen in a more controlled manner.

The multiple test applicator unit and the fluid tray are preferably made of engineering grade polymers that are sterilized prior to use in an autoclave, or other standard sterilization procedures. Hence, the materials preferably are made of plastics that are stable at higher temperatures. The multiple test applicator unit is depicted having ten scratching barbs. The multiple applicator unit may also have two, four, six, eight, twelve, and any of a wide variety of configurations, as needed.

It is critical during use that the allergens for the various reservoirs do not become intermixed as this contamination will affect the test results. The suggested minimum distance between two neighboring scratching barbs extending from the same side frame is preferably at least three-quarters of an inch.

It is critical that the multiple test applicator unit be held in one hand of the medical technician who is administering the test. This will enable the other hand to be free to take notes, to assist the patient, or do whatever becomes necessary during the administration of the procedure.

Accordingly, the multiple test applicator unit having ten scratching barbs as depicted is preferably about 2" (height)× 2" (width)×5" (length). If the multiple test applicator has eight scratching barbs (2×4), the length is preferably 3.75" to 4.50" in length, if the multiple test applicator has twelve scratching barbs (2×6), the length is about 5.00 to 5.50", etc. It is to be understood that while the multiple allergen testing device of the present invention as depicted in the accompanying drawings depicts a unit with ten testing devices, one skilled in the art can readily modify this geometry to include 4, 6, 8, 12, 16, 20, 24, 30, 36, or any other combination of multiple testing devices, this disclosure is being limited to 10 for purposes of illustration only.

Allergens are inserted into containment reservoirs in the loading tray (the trays may also be preloaded). The multiple test applicator [10] is removed from its sterile package. The applicator is removed from the fluid tray [50] and placed onto the skin of the patient [90]. The testing arms are pulled toward the center of the applicator from both sides, raising up the skin of the patient. The pair of skin lifting pads [45] are sandwiched about each scratching barb [61]. The scratching barbs [61] lift the skin and limit the depth of penetration of each scratching barb [61]. From this position, the scratching barb [61] is pulled up and away from the skin of the patient [90]. This action creates a small scratch [91] on the skin of the patient [90] inserting a small amount of allergen [57] under the skin.

The multiple test applicator of the present invention [10] enables testing for multiple allergies in one device and one test procedure or one test with the single tester and one allergy testing fluid. The most consistent results have been achieved by inserting a drop of allergy testing fluid on the skin and then scratching the skin with a simple needle (best practice). The multiple test applicator of the present invention [10] duplicates the best practice but in a controlled, repeatable, and reproducible way. The system built around the devices of the present invention enables the accurate and repeatable placement of the allergy testing fluid, in a tray and transfers this fluid to the multiple test applicator of the present invention [10] or the single test applicator [180], by placing the testing end of the device, into the fluid tray [50].

The multiple test applicator of the present invention [10] is removed from the fluid tray [50] and placed on the skin of the patent [90]. The testing arms are pulled toward the center of the multiple allergen testing device from both sides, lifting the skin up. From this position, the applicator [10] is pulled up and away from the skin [90]. This action generates a small scratch [91] on the skin of the patient [90] and moves a trace amount of allergen [57] under the skin of the patient [90].

The scratching barb [61] is subsequently transferred to the skin of the patient [90]. Once the scratching barb [61] of the multiple test applicator of the present invention [10] is on the skin of the patient, the applicator [10] is moved in such a way, as to lift the skin in front of the scratching barb [61]. The next action is to lift the multiple test applicator of the present invention [10] perpendicular to the skin of the patient [90], causing the scratching barb [61], which is immersed in allergen [57], to scratch the skin through the epidermis in a way so not to penetrate the dermis.

After the prescribed time 10-20 minutes the test operator records the skin condition. The Applicator includes break-off features for the arms, legs, and tips enabling more efficient disposal of the device after use with a patient. The break-off features for the tips enable this part of the applicator to be disposed of in a biohazard sharps container. The leg break-off points enable the legs to be broken off from the spine and the legs and spine to be disposed of in a separate container from the tips. The testing tray can also be disposed of in the same container. This increases the packing density of the discarded material and a much lower disposal cost.

Also, the multiple test applicator of the present invention has the advantage of breaking the skin of the patient without downward pressure. This diminishes chances of the mast cells (histamine containing cells) releasing the histamine secondary to pressure causing a false positive. This may be a critical factor with percutaneous allergy testing.

Throughout this application, various Patents and Applications are referenced by number and inventor. The disclosures of these documents in their entireties are hereby incorporated by reference into this specification in order to more fully describe the state of the art to which this invention pertains.

It is evident that many alternatives, modifications, and variations of the multiple allergen test applicator of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10. Multiple Test Applicator—1$^{st}$ Embodiment
20. Multiple Allergen Testing System—1$^{st}$ Embodiment
21. Spine
22. Spine Arm
30. and 31. Side Frame/Handle
32. Handle Arm
35. and 36. Finger Grip
44. Barb Break-Off
45. Skin Lifting Pad
46. Channel
47. Aperture
48. Vial
50. Fluid Tray—1$^{st}$ Embodiment
54. Reservoir
57. Allergen
61. Scratching Barb
62. Scratching Barb
63. Scratching Barb
90. Skin of Patient
91. Scratch
94. Raised Skin
110. Multiple Test Applicator—2$^{nd}$ Embodiment
120. Multiple Allergen Testing System—2$^{nd}$ Embodiment
180. Single Unit Applicator
210. Multiple Allergen Testing System—3$^{rd}$ Embodiment
220. Multiple Test Applicator—3$^{rd}$ Embodiment
261. Scratching Barb
262. Scratching Barb
263. Scratching Barb

I claim:

1. A multiple test applicator for administering onto skin of a patient a first and a second allergen used in allergy skin testing, said multiple test applicator including:
    a first scratching barb being cooperatively engageable with a first reservoir on a fluid tray as a second scratching barb is cooperatively engageable with a second reservoir on said fluid tray, said fluid tray having said first allergen retainable in said first reservoir and said second allergen retainable in said second reservoir, said multiple test applicator having an expanded position and a compressed position, said first scratching barb retaining some of said first allergen when removed from said first reservoir as said second scratching barb retains some of said second allergen when removed from said second reservoir during allergen loading; and
    a first side handle and a second side handle, a first finger grip being disposed on said first side handle, a second finger grip being disposed on said second side handle, said first finger grip opposing said second finger grip, a squeezing together of said first finger grip and said second finger grip using only one hand decreases the distance between said first scratching barb and said second scratching barb, during allergen deposition said first scratching barb generating a first scratch onto said skin of said patient as said first allergen is deposited into said first scratch, while said second scratching barb generates a second scratch onto said skin of said patient as said second allergen is deposited into said second scratch.

2. The multiple test applicator of claim 1, wherein said multiple test applicator is in said expanded position during said allergen loading and in said compressed position during allergen deposition.

3. The multiple test applicator of claim 1, wherein said first scratching barb is positioned farther away from said second scratching barb during said allergen loading than during said allergen deposition.

4. The multiple test applicator of claim 1, wherein said first and second scratching barbs project upward when positioned in said fluid tray.

5. The multiple test applicator of claim 1, wherein said first scratching barb moves away from said second scratching barb during said allergen deposition.

6. The multiple test applicator of claim 1, wherein said multiple test applicator being-cooperatively engageable with a single test applicator and said fluid tray for testing a single allergen, said single test applicator including a single scratching barb, said single scratching barb retaining some of a single allergen when removed from a single reservoir of said fluid tray, said multiple test applicator enabling testing of said first allergen, said second allergen, and said single allergen in one device.

7. The multiple test applicator of claim 1, wherein after completion of allergen loading in said expanded position, said first scratching barb and said second scratching barb are removed from said fluid tray and said multiple test applicator is moved into said compressed position and placed on said skin of said patient and released.

8. A multiple test applicator for administering onto skin a patient a first and a second allergen used in allergy skin testing, said multiple test applicator comprising:
    a first scratching barb cooperatively engageable with a first reservoir in a fluid tray, said fluid tray having said first allergen retainable in said first reservoir, said first scratching barb pointing upwards when disposed in said fluid tray, said first scratching barb retaining some of said first allergen when removed from said first reservoir during allergen loading; and
    a second scratching barb cooperatively engageable with a second reservoir in said fluid tray, said fluid tray having said second allergen retainable in said second reservoir, said second scratching barb pointing upwards when disposed in said fluid tray, said multiple test applicator having an expanded position and a compressed position, during allergen deposition said first scratching barb generating a first scratch on said skin of said patient as said first allergen is deposited into said first scratch while said second scratching barb generates a second scratch onto said skin of said patient as said second allergen is deposited into said second scratch.

9. The multiple test applicator of claim 8, wherein said first scratching barb is positioned farther away from said second scratching barb during said allergen loading than during said allergen deposition.

10. The multiple test applicator of claim 8, wherein said first scratching barb is sandwiched between a pair of skin lifting pads.

11. The multiple test applicator of claim 8, wherein said multiple test applicator has an expanded position and a compressed position, said multiple test applicator is in said expanded position during said allergen loading, said multiple test applicator being in said compressed position during said allergen deposition.

12. The multiple test applicator of claim 8, wherein said multiple test applicator has an expanded position and a compressed position, said first scratching barb being disposed nearer said second scratching barb in said compressed position, said first scratching barb being disposed farther from said second scratching barb in said expanded position.

13. The multiple test applicator of claim 8, wherein said multiple test applicator being cooperatively engageable with a single test applicator and said fluid tray, said single test applicator including a single scratching barb, said single scratching barb retaining some of a single allergen when removed from a single reservoir of said fluid tray, said multiple test applicator enabling testing of said first allergen, said second allergen, and said single allergen in one device.

14. The multiple test applicator of claim 8, further comprising a first side handle and a second side handle, a first finger grip being disposed on said first side handle, a second finger grip being disposed on said second side handle, said first finger grip opposing said second finger grip, said multiple test applicator having an expanded position and a compressed position, a squeezing together of said first finger grip and said second finger grip using only one hand decreases the distance between said first scratching barb and said second scratching barb.

15. A multiple test applicator for administering onto skin of a patient a first and a second allergen used in allergy skin testing, said multiple test applicator comprising:
a first scratching barb being cooperatively engageable with a first reservoir on a fluid tray, a first allergen being retainable in said first reservoir, said first scratching barb retaining some of said first allergen when removed from said first reservoir during allergen loading; and
a second scratching barb being cooperatively engageable with a second reservoir on said fluid tray, said fluid tray having a second allergen retainable in said second reservoir, said second scratching barb being disposed in said fluid tray during said allergen loading, said multiple test applicator having an expanded position and a compressed position, said multiple test applicator being in said expanded position during allergen loading, said multiple test applicator being in said compressed position during allergen deposition, during said allergen deposition said first scratching barb generating a first scratch onto said skin of said patient as said first allergen is deposited into said first scratch as said second scratching barb generates a second scratch onto said skin of said patient as said second allergen is deposited into said second scratch.

16. The multiple test applicator of claim 15, wherein said first and second scratching barbs project upward when compressed, said first scratching barb being sandwiched between a pair of skin lifting pads.

17. The multiple test applicator of claim 15, wherein said first scratching barb is positioned farther from said second scratching barb in said expanded position than in said compressed position.

18. The multiple test applicator of claim 15, further comprising a first side handle and a second side handle, a first finger grip being disposed on said first side handle, a second finger grip being disposed on said second side handle, said first finger grip opposing said second finger grip, a squeezing together of said first finger grip and said second finger grip using only one hand decreases the distance between said first scratching barb and said second scratching barb.

19. The multiple test applicator of claim 15, wherein said first scratching barb moves away from said second scratching barb during said allergen deposition.

20. The multiple test applicator of claim 15, wherein said multiple test applicator being cooperatively engageable with a single test applicator and said fluid tray, said single test applicator including a single scratching barb, said single scratching barb retaining some of a single allergen when removed from a single reservoir of said fluid tray, said multiple test applicator enabling testing of said first allergen, said second allergen, and said single allergen in one device.

21. The multiple test applicator of claim 15, wherein said expanded position and said compressed position of said multiple test applicator facilitate movement of said multiple test applicator from said expanded position during allergy loading to said compressed position prior to placement onto said skin of said patient.

22. A multiple test applicator for administering onto skin a patient a first and a second allergen used in allergy skin testing, said multiple test applicator comprising:
a first scratching barb being cooperatively engageable with a first reservoir on a fluid tray, said fluid tray having said first allergen retainable in said first reservoir; and
a second scratching barb being cooperatively engageable with a second reservoir on said fluid tray as said first scratching barb is cooperatively engageable with said first reservoir on said fluid tray, said second allergen being retainable in said second reservoir, said multiple test applicator having an expanded position and a compressed position facilitating movement of said multiple test applicator from said expanded position during allergy loading to said compressed position prior to placement onto said skin of said patient, during said allergen deposition said first scratching barb generating a first scratch onto said skin of said patient as said first allergen is deposited into said first scratch as said second scratching barb generates a second scratch onto said skin of said patient as said second allergen is deposited into said second scratch.

23. The multiple test applicator of claim 22, wherein said first scratching barb moves away from said second scratching barb as said first scratch and said second scratch are formed.

24. The multiple test applicator of claim 22, wherein said first scratching barb opposes said second scratching barb, said first scratching barb moving toward said second scratching barb when said multiple test applicator changes from said expanded position to said compressed position.

25. The multiple test applicator of claim 22, further comprising a first side handle and a second side handle, a first finger grip being disposed on said first side handle, a second finger grip being disposed on said second side handle, said first finger grip opposing said second finger grip, a squeezing together of said first finger grip and said second finger grip using only one hand decreases the distance between said first scratching barb and said second scratching barb.

26. The multiple test applicator of claim 22, wherein said first scratching barb is positioned farther away from said second scratching barb during said allergen loading than during said allergen deposition.

27. The multiple test applicator of claim 22, wherein said multiple test applicator is in said expanded position during said allergen loading, said multiple test applicator being in said compressed position during said allergen deposition.

28. The multiple test applicator of claim 22, wherein said multiple test applicator being cooperatively engageable with a single test applicator and said fluid tray, said single test applicator including a single scratching barb, said single scratching barb retaining some of a single allergen when removed from a single reservoir of said fluid tray, said multiple test applicator enabling testing of said first allergen, said second allergen, and said single allergen in one device.

\* \* \* \* \*